United States Patent [19]

Martin et al.

[11] Patent Number: 4,577,028
[45] Date of Patent: Mar. 18, 1986

[54] 5-HALOALKYL-PYRIDINES

[75] Inventors: Pierre Martin, Rheinfelden; Eginhard Steiner, Füllinsdorf, both of Switzerland

[73] Assignee: Ciba-Geigy Corporation, Ardsley, N.Y.

[21] Appl. No.: 434,433

[22] Filed: Oct. 14, 1982

[30] Foreign Application Priority Data

Oct. 20, 1981 [CH] Switzerland ............... 6692/81
Dec. 29, 1981 [CH] Switzerland ............... 8328/81
Sep. 1, 1982 [CH] Switzerland ............... 5195/82

[51] Int. Cl.⁴ .................. C07D 213/26; C07C 47/14
[52] U.S. Cl. .................. 546/345; 546/346; 546/300; 568/458; 568/495
[58] Field of Search ............... 546/345, 250, 346; 568/495, 458

[56] References Cited

U.S. PATENT DOCUMENTS

| | | | |
|---|---|---|---|
| 4,173,637 | 11/1979 | Nishiyama et al. | 546/300 X |
| 4,173,638 | 11/1979 | Nishiyama et al. | 546/300 X |
| 4,184,041 | 1/1980 | Nishiyama et al. | 546/345 |
| 4,205,175 | 5/1980 | Bowden et al. | 546/345 |
| 4,245,098 | 1/1981 | Steiner et al. | 546/250 |
| 4,260,766 | 4/1981 | Morris | 546/345 |
| 4,435,573 | 3/1984 | Lysenko et al. | 546/250 |
| 4,468,354 | 8/1984 | Lysenko et al. | 546/250 X |
| 4,469,896 | 9/1984 | Steiner et al. | 568/495 |
| 4,474,602 | 10/1984 | Markley et al. | 71/94 |

OTHER PUBLICATIONS

Huff et al., Helv. Chim. Acta., 60 (1977), pp. 907-921.
Noller, Textbook of Organic Chemistry, 3rd ed., W. B. Saunders Co., Philadelphia 1966, p. 619.
Klingsberg, Pyridine and Its Derivatives, Interscience Publishers, Inc., N.Y. 1961, pp. 338 & 288.

*Primary Examiner*—Joseph Paul Brust
*Attorney, Agent, or Firm*—Edward McC. Roberts; Bruce M. Collins

[57] ABSTRACT

Novel 5-haloalkyl-pyridines suitable for producing pesticidal compositions, particularly insecticides, and corresponding to the formula

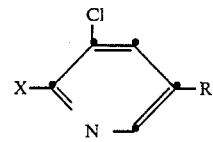

wherein R is a $C_2$-$C_{10}$-alkyl group which is uniformly or nonuniformly substituted by 1 to 21 halogen atoms, and X is halogen;

processes for producing them, as well as to the novel starting products and intermediates used or intermediately produced or formed in the production processes.

12 Claims, No Drawings

5-HALOALKYL-PYRIDINES

The invention relates to novel substituted 5-haloalkyl-pyridines and to processes for producing them, as well as to the therein intermediately produced or formed novel intermediates.

The novel 5-haloalkyl-pyridines correspond to the formula I

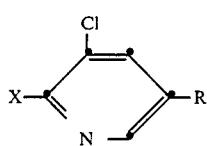

(I)

wherein R is a $C_2$–$C_{10}$-alkyl group which is uniformly or nonuniformly substituted by 1 to 21 halogen atoms, and X is halogen.

By halogen atoms or halogen is meant preferably fluorine, chlorine or bromine.

To be emphasised are those compounds of the formula I wherein R is an ethyl group which is uniformly or nonuniformly substituted by 1 to 5 fluorine or chlorine atoms, and X is fluorine or chlorine; particularly those compounds wherein R is a radical from the group comprising: —$CH_2$—$CF_3$, —$CF_2$—$CF_2Cl$, —$CF_2$—$CFCl_2$, —$CCl_2$—$CCl_3$, —$CF_2$—$CCl_3$, —$CF_2$—$CH_3$, —$CCl_2$—$CH_3$, —$CF_2$—$CF_3$, —$CH_2$—$CH_2Cl$, —$CH_2$—$CHCl_2$ or —$CH_2$—$CCl_3$.

Compounds of the formula I especially preferred are those wherein X is chlorine.

The compounds of the formula I can be used as starting products to produce, by way of one or more intermediate stages, various active substances, in particular active substances for plant protection, for example insecticides, herbicides or fungicides.

It is e.g. possible to obtain, starting with compounds of the formula I, valuable insecticides of the formula

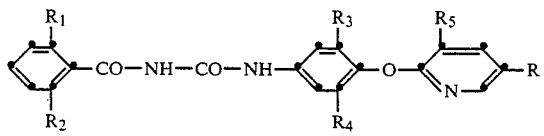

in which $R_1$ and $R_2$ are hydrogen, methyl or halogen, $R_3$ and $R_4$ are hydrogen or halogen, $R_5$ is chlorine, and R has the meaning defined under the formula I.

Chloropyridines substituted by trichloromethyl or trifluoromethyl groups could hitherto be produced only by complicated, multistage processes. On chlorination of 3-methylpyridine, there are in general formed several isomers in addition to the desired compound. By chlorination of 2,3-dichloro-5-methylpyridine is obtained 2,3-dichloro-5-trichloromethylpyridine, which can be converted, by exchange of the chlorine atoms of the trichloromethyl group for fluorine atoms, into 2,3-dichloro-5-trifluoromethyl-pyridine (cp., for example, European Patent Publication No. 004414). There are produced in a similar manner, according to the German Offenlegungsschrift No. 2,812,607, 2-halo-5-trifluoromethylpyridines and 2,3-dichloro-5-trifluoromethylpyridine. Halogen-substituted 5-trifluoromethyl- and 5-difluoromethylpyridines and the production thereof are known moreover from the published British Patent Application No. 2,002,368.

The compounds of the formula I are produced according to the invention by reaction of an aldehyde of the formula II with acrylonitrile, whereby there is firstly formed, by an addition reaction, an intermediate of the formula III, which is then cyclised—optionally in situ—to a pyridine compound of the formula I.

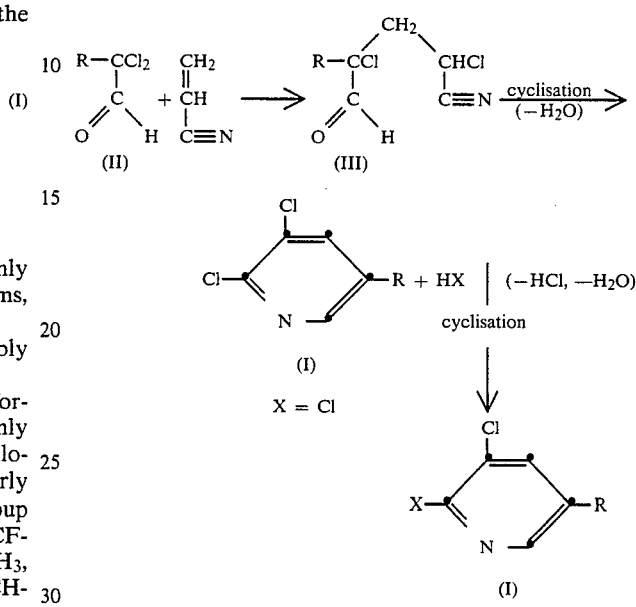

As is seen from the above reaction scheme, there are obtained, when the procedure is carried out in situ, that is, without isolation of the intermediate of the formula III wherein X is chlorine, compounds of the formula I in which X is chlorine. In case when an intermediate of the formula III is isolated, there is the possibility of reacting it with a hydrogen halide HX to obtain a compound of the formula I wherein X can not only be chlorine but also fluorine or bromine. Furthermore, a resulting compound of the formula I can be optionally further halogenated, preferably chlorinated, in the radical R, or halogen atoms present in the radical R can be exchanged for other halogen atoms, preferably chlorine for fluorine atoms, in order to obtain corresponding further compounds of the formula I. In the above formulae II and III, the symbol R has the meaning given under the formula I.

Aldehydes of the formula II wherein R is any one of the radicals —$CH_2$—$CCl_3$, —$CH_2$—$CHCl_2$ or —$CH_2$—$CH_2Cl$ are preferred as starting products. The pyridines of the formula I, obtained from these preferred aldehydes by an addition reaction with acrylonitrile and cyclisation of the addition product of the formula III, can be chlorinated in a particularly advantageous manner to 2,3-dichloro-5-(pentachloroethyl)-pyridine, whereupon, in the case of the last-mentioned compound, chlorine atoms present in the pentachloroethyl side chain can be exchanged preferably for fluorine atoms by means of customary fluorination methods. The number of fluorine atoms introduced by exchange depends on the selected fluorination conditions.

A structurally similar reaction sequence of trichloroformylbutyronitrile to 2,3,5-trichloropyridine is described in the European Patent Publication No. 12117. The cyclisation according to the invention with formation of an aromatic ring to give pyridines of the formula I was however not to be expected. Rather would the formation of a 2-pyridone derivative have been expected. The course of reaction according to the invention is thus to be described as being to a very great extent surprising.

The aldehydes of the formula II and the processes for producing them, insofar as they are novel, likewise from subject matter of the present invention. Novel aldehydes of the formula II can be obtained by reaction of trichloroacetaldehyde with corresponding ethylenically unsaturated compounds, for example

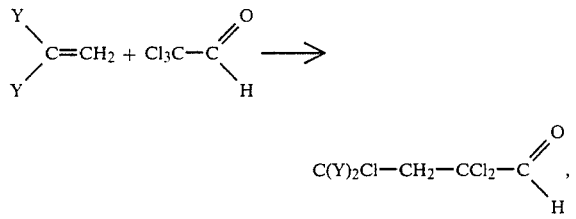

wherein Y is hydrogen or halogen, preferably chlorine.

The addition reactions with the formation of a compound of the formula III can be performed in an open or closed system, preferably at a temperature of 70°–160° C. The addition reaction is preferably carried out in a closed system under a pressure corresponding to the applied reaction temperature, the pressure being for example within the range of 1–30 bar.

Catalysts used for the addition reactions can be, according to the invention, metals of the main group VIII and of the subgroups VIa, VIIa, IB and IIb of the periodic system, for example iron, cobalt, nickel, ruthenium, palladium, chromium, molybdenum, manganese, copper and zinc. These metals can be employed in the elementary form or in the form of suitable compounds, for example oxides and salts, such as halides, sulfates, sulfites, sulfides, nitrates, acetates, stearates, citrates, carbonates, cyanides and rhodanides, as well as complexes with ligands, such as phosphines, phosphites, benzoyl- and acetylacetonates, nitriles, isonitriles and carbon monoxide.

Examples which may be mentioned are: copper(II) oxide or iron(III) oxide; copper(I)-, copper(II)-, iron(II)- and iron(III)-bromides, -iodides and particularly -chlorides, zinc chloride, as well as the chlorides of ruthenium, rhodium, palladium, cobalt and nickel; copper(II) sulfate, iron(II)- and iron(III)-sulfate; copper(II) nitrate and iron(III) nitrate; manganese(III) acetate, copper(II) acetate, copper(II) stearate, iron(III) citrate and copper(I) cyanide; ruthenium(II) dichloro-tris-triphenylphosphine, rhodium dichloro-tris-triphenylphosphine; chromium- and nickel-acetylacetonate, copper(II) acetylacetonate, iron(III) acetylacetonate, cobalt(II)- and cobalt(III)-acetylacetonate, manganese(II) acetylacetonate and copper(II) benzoylacetonate; iron carbonyl-cyclopenta-dienyl complex; molybdenum carbonylcyclopentadienyl complex, chromium tricarbonylaryl complexes, ruthenium(II) acetate complex, chromium- and molybdenum hexacarbonyl, nickel tetracarbonyl, iron pentacarbonyl and cobalt- and manganese-carbonyl.

It is also possible to use mixtures of the stated metals with metal compounds and/or other additives, such as copper powder in combination with one of the aforementioned copper compounds; mixtures of copper powder with lithium halides, such as lithium chloride, or isocyanides, such as tert-butylisocyanide; mixtures of iron powder with iron(III) chloride, optionally with the addition of carbon monoxide; mixtures of iron(III) chloride with benzoin; mixtures of iron(II)- or iron(III) chloride with trialkylphosphites; and mixtures of iron pentacarbonyl and iodine.

Particularly preferred are: copper powder, copper bronze, copper(I) chloride, and iron(II)- and iron(III)-chloride, as well as iron powder; ruthenium(III) chloride, ruthenium(II) dichloro-tris-triphenylphosphine, copper powder, copper bronze, copper(I)- and copper(II)-salts and -complexes, such as copper(I) chloride, copper(II) chloride, copper(I) bromide and copper(II) bromide; copper(II) acetate, copper(II) acetylacetone, copper(II) benzoylacetonate, copper(II) sulfate, copper(II) nitrate copper(I) cyanide and copper(I) iodide.

More particularly preferred are: copper powder, copper bronze, copper(I)- and copper(II) chloride and -bromide and copper(I) iodide, as well as mixtures thereof with one another.

The catalysts are in general used in amounts of about 0.01 to 10 mol %, preferably 0.1 to 5 mol %, relative to the aldehyde.

The addition reaction of the aldehydes of the formula II with acrylonitrile is advantageously performed in the presence of an inert organic solvent. Suitable solvents are those in which the catalysts are sufficiently soluble, or those which can form complexes with the catalysts, which solvents are however inert to the reactants. Examples of suitable solvents are: alkanecarboxylic acid nitriles, especially those having 2–5 carbon atoms, such as acetonitrile, propionitrile and butyronitrile; 3-alkoxy-propionitriles having 1–2 carbon atoms in the alkoxy group, such as 3-methoxypropionitrile and 3-ethoxypropionitrile; aromatic nitriles, particularly benzonitrile; aliphatic ketones having preferably a total of 3–8 carbon atoms, such as acetone, diethyl ketone, methylisopropyl ketone, diisopropyl ketone or methyl-tertbutyl ketone; alkyl and alkoxyalkyl esters of aliphatic monocarboxylic acids having in all 2–6 carbon atoms, such as formic acid-methyl and -ethyl esters, acetic acid-methyl, -ethyl, -n-butyl and -isobutyl esters, as well as 1-acetoxy-2-methoxyethane; cyclic ethers, such as tetrahydrofuran, tetrahydropyrane and dioxane; dialkyl ethers having 1–4 carbon atoms in each of the alkyl groups, such as diethyl ether, di-n-propyl ether and diisopropyl ether; N,N-dialkylamides of alkanecarboxylic acids having 1–3 carbon atoms in the alkyl group, such as N,N-dimethylformamide, N,N-dimethylacetamide, N,N-diethylacetamide and N,N-dimethylmethoxyacetamide; ethylene glycol and diethylene glycol dialkyl ethers having 1–4 carbon atoms in each of the alkyl groups, such as ethylene glycol dimethyl ether, -diethyl ether and -di-n-butyl ether; diethylene glycol diethyl ether and -di-n-butyl ether; phosphoric acid-tris-N,N-dimethylamide (Hexametapol). It is also possible to use excess acrylonitrile as solvent.

Preferred solvents for the addition reaction are alkanecarboxylic acid nitriles having 2–5 carbon atoms, and 3-alkoxypropionitriles having 1–2 carbon atoms in the alkoxy group, especially acetonitrile, butyronitrile and 3-methoxypropionitrile, or the acrylonitrile used as reactant.

The addition products of the formula III are novel; they have been developed for the synthesis of the compounds of the formula I, and they likewise form subject matter of the present invention.

The cyclisation of the compounds of the formula III can be performed in an open or closed system at temperatures of between about 0° and 220° C., in particular between about 100° and 200° C. The cyclisation is performed preferably in an open system, in which case it is advantageous to carry out the reaction in the presence of a hydrogen halide, or in the presence of substances which form hydrogen halides under the reaction conditions, such as phosgene, boron trichloride, aluminium chloride, trialkylammonium chlorides having 1–4 carbon atoms in each of the alkyl groups, phosphorus pentachloride, phosphorous oxychloride or phosphorus trichloride, or the corresponding bromine or fluorine compounds. The cyclisation reaction is preferably performed in the presence of hydrogen chloride, hydrogen bromide or hydrogen fluoride.

The cyclisation reaction is preferably performed without the addition of a solvent, in the liquid or gas phase, by merely heating the compounds of the formula III. The reaction can however also be performed in the presence of an organic solvent. Suitable organic solvents are for example chlorinated aliphatic hydrocarbons, such as chloroform, methylene chloride and tetrachloroethane; optionally chlorinated aromatic hydrocarbons, such as benzene, toluene, xylenes and chlorobenzenes; N,N-dialkylamides of alkane carboxylic acids having 1–3 carbon atoms, such as N,N-dimethylformamide, N,N-dimethylacetamide, N,N-diethylacetamide and N,N-dimethylmethoxyacetamide; cyclic amides, such as N-methyl-2-pyrrolidone, N-acetyl-2-pyrrolidone and N-methyl-ε-caprolactam; amides of carbonic acid, such as tetramethylurea and dimorpholinocarbonyl; amides or phosphorous acid, of phosphoric acid, of phenylphosphonic acid or of alkylphosphonic acids having 1–3 carbon atoms in the alkyl group, such as phosphoric acid triamide, phosphoric acid-tris-(N,N-dimethylamide), phosphoric acid trimorpholide, phosphoric acid tripyrrolinide, phosphoric acid-tris-(N,N-dimethylamide), methanephosphonic acid-bis-(N,N-dimethylamide); amides of sulfuric acid or of aliphatic or aromatic sulfonic acids, such as tetramethylsulfamide, methanesulfonic acid dimethylamide or p-toluenesulfonic acid amide; aliphatic ketones, cyclic ethers, dialkyl ethers, as well as ethylene glycol and diethylene glycol dialkyl ethers of the aforementioned type, and also phosphorus trichloride and phosphorus oxychloride.

Preferred solvents for the cyclisation reaction are chloroform, methylene chloride, cyclic ethers and dialkyl ethers having 1–4 carbon atoms in each of the alkyl groups, especially dioxane and diethyl ether, as well as N,N-dialkylamides of alkanecarboxylic acids having 1–3 carbon atoms, particularly N,N-dimethylformamide.

The process according to the invention can be advantageously performed by firstly isolating the compounds of the formula III formed by the addition reaction, and subsequently cyclising them in a second stage of the process. The individual process steps are carried out as described in the foregoing.

An advantageous embodiment of the process according to the invention comprises reacting an aldehyde of the formula II with acrylonitrile in a closed system, at a temperature of 70°–160° C., in acetonitrile, butyronitrile or 3-methoxypropionitrile as solvent, in the presence of 0.1–6 mol % of copper powder, copper bronze, copper-(I)- or copper(II)-chloride or -bromide or copper(I) iodide, or in the presence of a mixture of these substances. The compound of the formula III thus obtained after separation of the solvent is then cyclised at a temperature of between 100° and 200° C., in an open system, in the presence of a hydrogen halide, or of a substance that forms a hydrogen halide under the reaction conditions, to give a compound of the formula I.

It is possible however, when X is chlorine, to advantageously dispense with the isolation of the addition product of the formula III, and to perform the addition and cyclisation reactions in one operation. In this case, the reaction of the aldehyde of the formula II with acrylonitrile to a pyridine of the formula I is carried our preferably at a temperature of between 70° and 220° C., especially between 130° and 200° C. This process can be performed in an open or closed system. When the reaction is carried out in an open system, it can be advantageous to carry it out in the presence of hydrogen chloride, or of substances which form hydrogen chloride under the reaction conditions. These substances are for example phosgene, boron trichloride, aluminium chloride, trialkylammonium chloride having 1–4 carbon atoms in each of the alkyl groups, phosphorus pentachloride, phosphorus oxychloride or phosphorous trichloride. The single-stage production of pyridines of the formula I is preferably performed however in a closed system under a pressure corresponding to the applied reaction temperature, the pressure being for example within the range of 1–50 bar, depending on the reaction temperature. The single-stage synthesis of compounds of the formula I in a closed system at a pressure of 1–30 bar is especially preferred.

The said single-stage synthesis can likewise be carried out in the presence of a catalyst, and advantageously in the presence of an inert organic solvent. Suitable catalysts and solvents are those of the type described earlier in the text, and with regard to preferred catalysts and amounts of catalyst, that applies which was stated in the foregoing in this connection.

Preferred solvents for carrying out the process in a single-stage are alkanecarboxylic acid nitriles having 2–5 carbon atoms, and 3-alkoxypropionitriles having 1–2 carbon atoms in the alkoxy group. Particularly suitable solvents are acetonitrile, butyronitrile and 3-methoxypropionitrile, or an excess of the acrylonitrile used as reactant. After completion of the reaction, the chloropyridines of the formula I can be isolated in the customary manner, for example by removal of the solvent by evaporation, and purification of the crude product by distillation or by steam distillation.

A further advantageous embodiment of the process according to the invention comprises reacting the aldehydes of the formula II and the acrylonitrile directly to the pyridines of the formula I, the reaction being performed at 130°–200° C. in acetonitrile, butyronitrile or 3-methoxypropionitrile as solvent, in the presence of 0.1 to 6 mol % of copper powder, copper bronze, copper-(I)- or copper(II)-chloride or -bromide or copper(I) iodide, or of a mixture of these substances, and in a closed system under a pressure corresponding to the applied reaction temperature.

The compounds of the formula I produced by the process described in the foregoing can be optionally converted by further halogenation of the side-chain group R present on the pyridine ring, or by exchange of the halogen atoms present in this group R for other halogen atoms, into different compounds of the formula I within the scope of the present invention. These halogenation and halogen-exchange reactions are performed by methods known per se. Thus, for example, hydrogen atoms present in the group R can be exchanged for halogen atoms by means of halogenation reactions, for example by chlorination or bromination. The halogen exchange reactions in the R group are performed preferably for the purpose of introducing fluorine atoms, for example by the exchange of halogen atoms, for example chlorine atoms, for fluorine atoms with the use of suitable metal fluorides.

EXAMPLE 1

(Production of the starting compounds)

Production of 2,2,4,4,4-pentachlorobutyraldehyde (a) Into 200 ml of dimethylformamide are introduced, with cooling, 10 g of HCl gas and afterwards, at 60°–65° C., 10 g of chlorine. There is then added dropwise to the slightly yellow solution, likewise at 60°–65° C., the solution of 210 g of 2,4,4,4-tetrachlorobutyraldehyde in 300 ml of dimethylformamide, and simultaneously an approximately aliquotic amount of chlorine is introduced until the reaction solution remains slightly yellow. The temperature is maintained for 1 hour at 65° C., and the reaction mixture is subsequently subjected to steam distillation. The organic phase of the distillate is separated, and rectified in vacuo, and the light-yellow oil, b.p.$_{15\ mm}$ 95°–99° C., is collected.

(b) 145.3 g of vinylidene chloride, 148.0 g of trichloroacetaldehyde, 3.0 g of copper(I) chloride and 300 ml of acetonitrile are heated in an enamelled autoclave at 125° C. for 12 hours. The solvent is thereupon distilled off in a water-jet vacuum, and the residue is taken up in 500 ml of diethyl ether. After removal of precipitated copper sludge by filtration, the diethyl ether is distilled off, and the residue is rectified in a water-jet vacuum to thus obtain the title compound, b.p.$_{15\ mm}$ 95°–99° C.

Production of 2,2,4,4-tetrachlorobutyraldehyde 125.0 g of vinyl chloride, 148.0 g of trichloroacetaldehyde, 3 g of copper(I) chloride and 300 ml of acetonitrile are heated in an enamelled autoclave for 4 hours at 140° C. After cooling, the solvent is distilled off at room temperature in a water-jet vacuum. The residue is taken up in 500 ml of diethyl ether, and filtered off from the precipitated copper(I) chloride. The diethyl ether is distilled off, and the residue is rectified in a water-jet vacuum. The product thus obtained is a colourless liquid, b.p.$_{12\ mm}$ 78°–80° C.

Production of 2,2,4-trichlorobutyraldehyde 56.1 g of ethylene, 148.0 g of trichloroacetaldehyde, 3.0 g of copper(I) chloride and 300 ml of acetonitrile are heated in an enamelled autoclave at 140° C. for 4 hours. After cooling, the solvent is distilled off at room temperature in a water-jet vacuum. The residue is taken up in 500 ml of diethyl ether, and filtered off from the precipitated copper(I) chloride. After the diethyl ether has been distilled off, the residue is rectified in a water-jet vacuum. There is obtained a colourless liquid, b.p.$_{15\ mm}$ 64°–66° C.

EXAMPLE 2

Production of 2,3-dichloro-5-(2,2,2-trichloroethyl)-pyridine 244.3 g of the 2,2,4,4,4-pentachlorobutyraldehyde produced according to Example 1, 110 g of acrylonitrile, 400 ml of acetonitrile and 5 g of CuCl are heated in a tantalum autoclave at 180° C. for 4 hours. After cooling, the acetonitrile and the excess of acrylonirile are distilled off in vacuo. The dark oil remaining is extracted with diethyl ether; the ether is then dried with Na$_2$SO$_4$, and evaporated off in vacuo, and the residue is subjected to steam distillation. The 2,3-dichloro-5-(2,2,2-trichloroethyl)-pyridine precipitates, in the distillate, in the form of almost white flakes. After a single recrystallisation from ethanol diluted with water, the product has a melting point of 98°–99° C.

EXAMPLE 3

Production of 2,3-dichloro-5-(2-chloroethyl)-pyridine 175.4 g of 2,2,4-trichlorobutyraldehyde together with 132.5 g of acrylonitrile, 400 ml of acetonitrile and 5 g of CuCl are heated in a tantalum autoclave within 3 hours to 180° C., and held for 2 hours at this temperature. After cooling, the acetonitrile and the excess of acrylonitrile are distilled off in vacuo. The dark oil remaining is extracted with diethyl ether; the ether is dried with Na$_2$SO$_4$ and then evaporated off in vacuo. The residue is subjected to steam distillation, and the 2,3-dichloro-5-(2-chloroethyl)-pyridine precipitates, in the distillate, in the form of a colourless oil. It is distilled under high vacuum and has a b.p.$_{0.1\ mm}$ of 97°–100° C.

EXAMPLE 4

Production of 2,3-dichloro-5-(pentachloroethyl)-pyridine (a) 279.4 g of 2,3-dichloro-5-(2,2,2-trichloroethyl)-pyridine are dissolved in 3 liters of carbon tetrachloride. Into this solution are introduced within about 1 hour, with cooling, 120 g of HCl gas, in the course of which the hydrochloride of the pyridine compound partially precipitates. The reaction mixture is heated to 50° C., and is then treated, whilst being exposed to light from a Hg high-pressure lamp (125 watt), with chlorine gas. The reaction solution is thereupon concentrated in vacuo, and the crystal sludge remaining is recrystallised from methanol. There are thus obtained colourless crystals of the title compound, m.p. 97.5°–98° C.

(b) 210.5 g of 2,3-dichloro-5-(2-chloroethyl)-pyridine (obtained according to Example 3) are chlorinated and further processed by the method given in the foregoing under (a). The product has a melting point of 97°–98° C. and is identical to that obtained above under (a).

(c) 244.9 g of 2,3-dichloro-5-(2,2-dichloroethyl)-pyridine (obtained according to the following Example 7) are chlorinated and further processed by the method described under (a). The product is identical to that obtained above under (a).

EXAMPLE 5

Production of 2,3-dichloro-5-(1,1,2,2-tetrafluoro-2-chloroethyl)-pyridine 348.2 g of 2,3-dichloro-5-(pentachloroethyl)-pyridine are melted together with 1000 g of antimony trifluoride and 30 g of antimony pentachloride for 2 hours at 210° C. After the melt has been cooled to 90° C., there are added 2 liters of water, and the whole is subjected to steam distillation. The colourless oil distilling over is separated, dried with Na$_2$SO$_4$ and then rectified in a water-jet vacuum. The product distilling at b.p.$_{11\ mm}$ 97°–100° C. is collected.

EXAMPLE 6

Production of 2,3-dichloro-5-(1,1,2-trifluoro-2,2-dichloroethyl)-pyridine

The distillation residue according to the preceding Example 5 is further distilled, and the product distilling at b.p.$_{11\ mm}$ 120°–122° C. is collected.

EXAMPLE 7

Production of 2,3-dichloro-5-(2,2-dichloroethyl)-pyridine

By replacing in Example 3 in the foregoing the 2,2,4-trichlorobutyraldehyde by 210.0 g of 2,2,4,4-tetrachlorobutyraldehyde, the procedure otherwise being the same, there is obtained 2,3-dichloro-5-(2,2-dichloroethyl)-pyridine in the form of white crystals, m.p. 89°–90° C.

Also the following compound of the formula I is obtainable by a procedure analogous to that described in the foregoing:

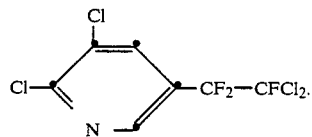

b.p.$_{0.01\ mm}$ 72°–73° C.—becomes crystalline on standing.

What is claimed is:

1. A compound of the formula:

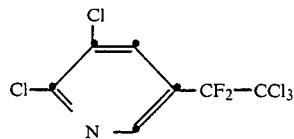

wherein R is mono-, poly- or perhalogenated alkyl group of 2 carbon atoms.

2. A compound according to claim 1 wherein R contains 2 carbon atoms and is halogenated with chlorine or fluorine.

3. A compound according to claim 1, wherein R is —CH$_2$—CF$_3$, —CF$_2$—CF$_2$Cl, —CF$_2$—CFCl$_2$, —CCl$_2$—CCl$_3$, —CF$_2$—CCl$_3$, —CF$_2$—CH$_3$, —CCl$_2$—CH$_3$, —CF$_2$—CF$_3$, —CH$_2$—CH$_2$Cl, —CH$_2$—CHCl$_2$ or —CH$_2$—CCl$_3$.

4. A compound according to claim 1 of the formula

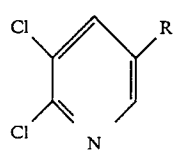

5. A compound according to claim 1 of the formula

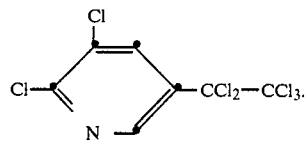

6. A compound according to claim 1 of the formula

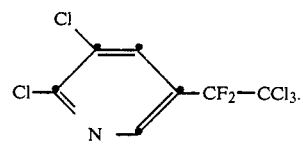

7. A compound according to claim 1 of the formula

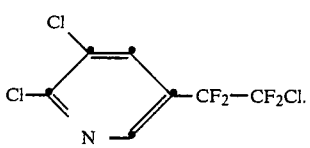

8. A compound according to claim 1 of the formula

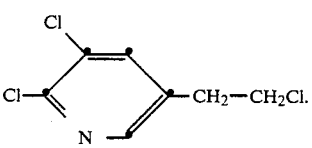

9. A compound according to claim 1 of the formula

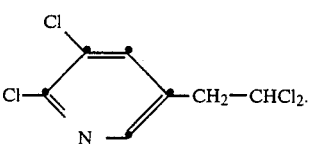

10. A compound according to claim 1 of the formula

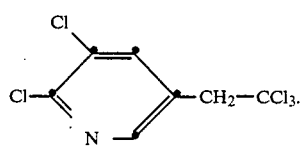

11. A compound selected from the group consisting of 2,2,4-trichlorobutyraldehyde, 2,2,4,4-tetrachlorobutyraldehyde and 2,2,4,4,4-pentachlorobutyraldehyde.

12. A process for the preparation of a compound selected from the group consisting of 2,2,4-trichlorobutyraldehyde, 2,2,4,4-tetrachlorobutyraldehyde or 2,2,4,4,4-pentachlorobutyraldehyde which comprising allowing trichloroacetaldehyde to react with ethylene, chloroethylene or 1,1-dichloroethylene, respectively.

* * * * *